United States Patent [19]

Homer et al.

[11] Patent Number: 4,977,254

[45] Date of Patent: Dec. 11, 1990

[54] PROCESS FOR THE CHLORINATION OF SUGARS

[75] Inventors: Nigel J. Homer; Graham Jackson; George H. Sankey, all of Reading; Philip J. Simpson, Tadley, all of Great Britain

[73] Assignee: Tate & Lyle PLC, United Kingdom

[21] Appl. No.: 388,657

[22] Filed: Aug. 2, 1989

[30] Foreign Application Priority Data

Aug. 3, 1988 [GB] United Kingdom ............... 8818430

[51] Int. Cl.$^5$ .................... C07H 1/00; C07H 15/00; C08B 37/00; C07G 3/00
[52] U.S. Cl. .................... 536/124; 536/122; 536/18.4; 536/18.5; 536/119; 536/115; 536/116; 536/120
[58] Field of Search .................. 536/124, 122, 18.4, 536/18.5, 119, 115, 120, 116

[56] References Cited

U.S. PATENT DOCUMENTS

| | | | |
|---|---|---|---|
| 4,362,869 | 12/1982 | Jenner et al. | 536/122 |
| 4,380,476 | 4/1983 | Mufti et al. | 536/122 |
| 4,751,294 | 6/1988 | Jackson | 536/122 |
| 4,783,526 | 11/1988 | O'Brien et al. | 536/18.4 |
| 4,826,962 | 5/1989 | Rathbone et al. | 536/122 |

FOREIGN PATENT DOCUMENTS

| | | |
|---|---|---|
| 2036007 | 6/1980 | United Kingdom ............... 536/122 |
| 2104063 | 3/1983 | United Kingdom ............... 536/122 |
| 2181734 | 4/1987 | United Kingdom . |
| 2182039 | 5/1987 | United Kingdom . |

*Primary Examiner*—Ronald W. Griffin
*Assistant Examiner*—Everett White
*Attorney, Agent, or Firm*—Ostrolenk, Faber, Gerb & Soffen

[57] ABSTRACT

Sugars and partly protected sugar derivatives are chlorinated by reaction of unprotected hydroxyl groups with thionyl chloride to form a persulphite followed by decomposition of the sulphite groups to form chlorosulphites, displacement of the chlorosulphite groups and insertion of chlorine atoms at one or more positions, characterised in that formation and displacement of the chlorosulphite groups and insertion of chlorine atoms is effected by reaction with thionyl chloride in an inert solvent in the presence of a quaternary salt of the general formula:

$$N^+R^1R^2R^3R^4Cl^- \qquad (I)$$

wherein $R^1$, $R^2$ and $R^3$, which may be the same or different, each represent a lower alkyl group, and $R^4$ represents a hydrocarbon group with at least seven carbon atoms; and, when the sugar or partly protected sugar derivative has more than three unprotected hydroxyl groups, the process comprises the following stages:

(a) reaction of the sugar or partly protected derivative with thionyl chloride in the presence of pyridine to form a persulphite;

(b) isolation of the polysulphite to remove free pyridine; and (c) reaction of the isolated polysulphite with thionyl chloride in an inert solvent or suspension medium in the presence of a quaternary salt of the general formula (I).

14 Claims, No Drawings

PROCESS FOR THE CHLORINATION OF SUGARS

This invention relates to the chlorination of sugars to produce chlorodeoxy derivatives, and in particular to the chlorination of sugars and sugar derivatives in the preparation of chlorodeoxy sugar sweeteners such as sucralose (4,1',6-trichloro-4,1',6'-trideoxygalactosucrose) or its 6-chloro analogue 4,6,1',6'-tetrachloro-4,6,1',6'-tetradeoxygalactosucrose. The use of sucralose and other chlorodeoxy sucrose derivatives as sweeteners is disclosed in British Pat. Nos. 1 543 167 and 2 104 063 B.

Routes to sucralose (see, for example. Khan et al Carbohydrate Research. 39 (1975) 253; and Fairclough et al Carbohydrate Research, 40 (1975) 285–298, U.S. Pat. No. 4,362,869 and GB No. 2 065 648) involve the formation of derivatives of sucrose in which the 6-position is blocked so as to prevent chlorination in that position while the 4-, 1'- and 6'- positions are chlorinated. In the route of U.S. Pat. No. 4,362,869 and Fairclough et al., sucrose is tritylated in the three primary positions (6-, 1'- and 6'-) and then peracetylated. The trityl groups are then removed to provide the 2,3,4,3',4'-pentaacetate. The acetate at the 4- position is then caused to migrate to the 6- position, in the case of the patented process by treatment with dilute acetic acid in an inert solvent, so as to provide the 2,3,6,3',4'-pentaacetate (6-PAS) which can be chlorinated.

A number of different chlorinating methods are disclosed in U.S. Pat. No. 4,362,269. The chlorinating agent originally used in the preparation to sucralose was sulphuryl chloride in the presence of an organic amine base, such as pyridine. The problem with this process is that sulphuryl chloride tends to chlorinate the organic amine, especially pyridine, leading to the formation of unwanted by-products which are difficult to separate. Because of this, a number of other chlorinating reagents were proposed in the above mentioned patent. They include triarylphosphines with carbon tetrachloride in pyridine; Vilsmeier-type reagents formed by the reaction of an inorganic acid chloride such as phosphorus pentachloride, phosgene or thionyl chloride with an N,N-dialkylformamide or N,N-dialkylacetamide; and a triaryl dichlorophosphorane or triaryloxy dichlorophosphorane in pyridine.

Other chlorinating reagents proposed for this reaction include the use of thionyl chloride in the presence of a triarylphosphine oxide in an inert solvent such as toluene (GB No. 2 182 039 A).

Although there are thus a considerable number of methods of chlorinating 6-PAS, they all have certain drawbacks. When pyridine is used, wasteful side reactions between pyridine and the chlorinating agents commonly lead to the formation of by-products that are difficult to separate. Similarly, the use of Vilsmeier reagents is far from clean. Producing dark coloured reaction mixtures and intractable by-products. The triphenylphosphine oxide/thionyl chloride reagent can be used in an inert solvent such as toluene to give a much cleaner product with yields of up to 75%, but the process uses in excess of one molar equivalent (ME) of triphenylphosphine oxide (TPPO) per mole of 6-PAS, so that recovery of the TPPO is required for economical operation of the process. Further, removal of residues of TPPO from the chlorinated product can be difficult.

Another useful route to sucralose involves selective acylation of the 6- position of sucrose, followed by selective chlorination of the 4-, 1'- and 6'- positions in the presence of unprotected hydroxyl groups at the 2-, 3-, 3'- and 4'- positions (see, for example U.S. Pat. No. 4,380,475 and GB No. 2 079 749).

A related process is disclosed in GB No. 2 181 734 A. In this process, the 6-substituted sucrose is, in fact, the trisaccharide raffinose. Suitable chlorination of raffinose provides 6'',4,1',6'-tetrachloro-6',4,1'6'-tetradeoxygalactoraffinose, referred to for convenience as TCR. TCR can then be cleaved in the presence of a suitable α-galactosidase to yield sucralose.

The method of chlorinating raffinose disclosed in that specification involves the use of thionyl chloride in pyridine, in the presence of a triarylphosphine oxide or sulphide. Although this process gives the required chloro derivative, and in particular inserts a chlorine atom at the 4- position, it has considerable disadvantages. Firstly, the process employs three molar equivalents of the triaryl phosphine oxide or sulphide, especially three molar equivalents of triphenylphosphine oxide, which is troublesome to remove and (in the case of the oxide) to recycle. Secondly, the reaction conditions give rise to large amounts of black insoluble by-product leading to difficulties in the work-up. Thirdly, the yields are only moderate.

Similarly, in the case of the chlorination of sucrose 6-substituted sucrose derivatives, it is not easy to obtain the correct degree of chlorination and known systems involve the use of pyridine, with sulphuryl chloride (GB No. 2 079 749 B) or with thionyl chloride/TPPO (GB No. 2 195 632 A), or the use of Vilsmeier reagents (GB No. 2 079 749 B, GB No. 2 145 080 B), with attendant problems.

It has long been known that alcohols can be chlorinated by reaction with thionyl chloride and pyridine in the Darzens procedure (Darzens, Comptes Rendues, 1911, 152, 1314, 1601 and 1912, 154. 1615). The mechanism of the process was explained in some detail by Gerrard (Gerrard, J.Chem.Soc. 1939, 99; 1940, 218; and 1944, 85). In a first stage, two alcohol molecules ROH react with thionyl chloride to form a sulphite $R_2SO_3$ and two molecules of hydrogen chloride which react with the pyridine to form pyridine hydrochloride. In a second stage, the sulphite is decomposed by reaction with further thionyl chloride to provide two molecules of a chlorosulphite $RSO_2Cl$. In a third stage the chlorosulphites react with the pyridine hydrochloride to provide two molecules of chloride RCl and two molecules of sulphur dioxide.

Thus, in the Darzens process, pyridine acts as a solvent for the reactants, as an acid acceptor for the hydrogen chloride released during the initial reaction of thionyl chloride with the alcohol to form the sulphite and, in the form of pyridine hydrochloride, as a catalyst for the release of chloride ions for the last stage of the reaction. For polyhydroxy compounds where large quantities of hydrogen chloride are released, the action of pyridine as an acid acceptor prevents degradation of the polysulphite.

When this process is applied to polyhydroxy compounds such as sugars, it might be expected that intramolecular sulphites are produced, and in practice the result is always an exceedingly complex mixture of products. It is presumably for this reason that there appears to be no published example of the thionyl chloride-pyridine reagent system being used successfully to chlorinate sugars. The nearest approach is seen in the process of GB No. 2 181 734 A, which uses triphenyl phosphine oxide in conjunction with thionyl chloride and pyridine to chlorinate raffinose but, as mentioned above, the results are far from satisfactory.

We have now found an improved process for the chlorination of sugars and sugar derivatives which uses thionyl chloride in conjunction with an aralkyl quaternary ammonium chloride to obtain excellent yields of the desired chlorodeoxy sugar derivatives without generating intractable by-products. In this process, the aralkyl quaternary salt is used as a catalyst which provides a source of chloride ions to promote replacement of the chlorosulphites, formed by reaction of the intermediate persulphite with thionyl chloride, with chlorine atoms.

We have also found that it is important to ensure that reaction of the intermediate persulphite with thionyl chloride takes place in the absence of free pyridine, which otherwise would react with other components of the mixture to form undesirable by-products.

In the case of sugar derivatives in which many of the hydroxyl group are protected, e.g. as esters or ethers, it is not necessary to use pyridine as a solvent and acid acceptor during formation of the intermediate persulphite provided that a suitable catalyst, particularly the aralkyl quaternary salt mentioned above, is present in the reaction mixture. In such cases, therefore, the sugar derivative can simply be treated with thionyl chloride in an inert solvent in the presence of the catalyst.

In the case of sugars and sugar derivatives with many unprotected hydroxyl groups, however, where it is necessary to use pyridine in the first stage as an acid acceptor to prevent degradation of the intermediate polysulphite by hydrochloric acid released during its formation, the intermediate polysulphite must be isolated from free pyridine before reaction with thionyl chloride.

According to the invention there is therefore provided a process for the chlorination of sugars and partly protected sugar derivatives by reaction of unprotected hydroxyl groups with thionyl chloride to form a persulphite followed by decomposition of the sulphite groups to form chlorosulphites, displacement of the chlorosulphite groups and insertion of chlorine atoms at one or more positions, in which formation and displacement of the chlorosulphite group and insertion of chlorine atoms is effected by reaction with thionyl chloride in an inert solvent in the presence of a quaternary salt of the general formula:

  (I)

wherein $R^1$, $R^2$ and $R^3$, which may be the same or different, each represent a lower alkyl group, e.g. a methyl, ethyl or propyl group, and $R^4$ represents a hydrocarbon group with at least 7 carbon atoms, especially an arylalkyl group; and, when the sugar or partly protected sugar derivative has more than three unprotected hydroxyl groups, the process comprises the following stages:
  (a) reaction of the sugar or partly protected sugar derivative with thionyl chloride in the presence of pyridine to form a persulphite;
  (b) isolation of the polysulphite to remove free pyridine; and
  (c) reaction of the isolated polysulphite with thionyl chloride in an inert solvent or suspension medium in the presence of a quaternary salt of the general formula (I).

Salts of formula I are preferably benzylammonium salts e.g. benzyltrimethylammonium chloride, or, most preferably benzyltriethylammonium chloride (BETEC). We have tested related aryl and alkyl derivatives such as tetramethylammonium chloride and phenyltrimethylammonium chloride but these have little activity.

The amount of the quaternary salt of formula I needs only to be small because it acts as a catalyst, providing a chloride ion to attack the chlorosulphite to release sulphur dioxide and a chloride ion which then continues the reaction. In practice we find that about 0.2 to 0.4 ME. e.g. about 0.3 ME is suitable.

References throughout this specification to pyridine are to be taken to include pyridine analogues such as the picolines, luridines, and collidines. etc.

In the case of sugar derivatives having only a few unprotected hydroxy groups, e.g. 6-PAS, relatively small amounts of acid are released during formation of the persulphite and it is not actually necessary to use an acid acceptor such as pyridine in the first stage of the reaction. In such cases, we have found that it is possible to carry out an all-in-one reaction in which the starting material, thionyl chloride and the catalyst providing a source of chloride ions, i.e. a salt of formula I as defined above, are reacted in an inert solvent, e.g. toluene. In this reaction, the first two stages (sulphite and chlorosulphite) are carried out in the absence of an acid-acceptor such as pyridine but in the presence of the source of chloride ions which is then utilised in the third stage. A further advantage of using a salt of formula I is that it is readily water soluble and can thus be separated easily from the chlorinated sugar and recovered for re-use.

In general, we find that a relatively small excess of thionyl chloride is desirable, for example about 1.25 to 1.75 ME per free hydroxy group, i.e. 3.75 to 5.25 ME for 6-PAS; typically about 1.3 to 1.4 ME. i.e. 3.9 to 4.2 ME for 6-PAS.

In the case of sugars and sugar derivatives with many (more than three) unprotected hydroxyl groups where pyridine is used as a solvent and acid acceptor during formation of the intermediate polysulphite, it is necessary to isolate the intermediate to remove free pyridine before proceeding to the second stage.

Thus, if the sugar, particularly raffinose or a 6-protected sucrose, is reacted with a small excess of thionyl chloride in pyridine at a low temperature and the intermediate polysulphite so formed is then isolated from free pyridine, and is then subsequently reacted with thionyl chloride in the presence of a catalyst which acts as a source of chloride ions, cholorination occurs in a clean and regular manner. In particular, 6-substituted sucrose is chlorinated in the 4-, 1'-, and 6'- positions, with inversion of configuration at the 4position (as required for sucralose), and raffinose is chlorinated in the 6''-, 4-, 1'- and 6'- positions, again with inversion at the 4-position, to produce TCR.

The first stage of the process is thus to treat the sugar in pyridine and, optionally, another suitable solvent with thionyl chloride. The thionyl chloride should be present in a small to moderate excess, e.g. about a 10% excess. For example, raffinose which has 11 hydroxy groups would theoretically require 5.5 molar equivalents of thionyl chloride for complete sulphite formation. It is believed that the sulphite groups are intramolecular bridges, in the main, but it is possible that some inter molecular reaction also occurs. In the case of raffinose, we find that about 6 molar equivalents of thionyl chloride is enough.

Similarly, in the case of sucrose 6-acetate, a possible total of seven hydroxy groups are converted into sulphite groups with about 4 molar equivalents of thionyl chloride. Also sucrose, with eight hydroxy groups, can be reacted with 4.5 molar equivalents of thionyl chloride.

The second stage of the process then involves the separation of the sulphite intermediate from free-base pyridine. This is conveniently achieved by diluting the reaction mixture with a solvent system which dissolves pyridine but in which the sulphite intermediate (and, optionally, the pyridine hydrochloride) is insoluble. Suitable solvent systems include hydrocarbons such as light petroleum or toluene, and ethers such as diethyl ether, and mixtures thereof with polar solvents such as methanol.

Alternatively, the reaction mixture can be diluted with an alcohol such as methanol, in which the sulphite is insoluble. In either case, the solid material is then separated from the liquid and is washed with more of the solvent system and then dried in vacuo.

The third stage of the process comprises the treatment of the isolated sulphite, in the absence of pyridine, with more thionyl chloride in an inert solvent or suspension medium such as a halogenated hydrocarbon, e.g. 1,2-dichloroethane or an aromatic hydrocarbon such as toluene containing the source of chloride ions, especially a salt of formula I. The reaction is conveniently effected using an excess of thionyl chloride, e.g. 0.5 molar equivalent for every original hydroxyl group in the starting material, it being understood that not every hydroxyl group is necessarily replaced by chlorine in the reaction according to the invention, but only primary hydroxyl groups and some secondary hydroxyl groups. Thus, for example, sucrose 6-acetate is chlorinated at the 4, 1'- and 6'- positions required to produce sucralose. Similarly raffinose is chlorinated at the 6''-, 4-, 1'-, and 6'- positions required for TCR.

The second reaction with thionyl chloride, in the presence of the catalyst, is conveniently effected at an elevated temperature, e.g. the reflux temperature of the solvent, and the reaction mixture is then treated with a hydroxylic base such as aqueous methanolic ammonia to hydrolyse any unreacted sulphite and chlorosulphite groups to hydroxy groups.

The product can then be isolated in any convenient way. The conventional procedure is to peracetylate, isolate and de-acetylate, but sucralose can be isolated as sucralose itself, as the 6-acetate, or as the pentaacetate.

Thus, according to the present invention, sugar derivatives being either:
(a) polysulphites formed by reaction of sugars or sugar derivatives having more than three unprotected free hydroxyl groups with thionyl chloride and pyridine and then isolated from free base pyridine, or
(b) sugar derivatives having less than four unprotected free hydroxyl groups;

can be chlorinated by reaction with thionyl chloride in the presence of a salt of the formula I in an inert solvent.

The process is characterised by the absence of expensive co-reactants or of intractable by-products and by good yields of the required chlorosugars. It represents a particularly useful step in the production of sucralose.

The following examples illustrate the invention further:

In the Examples all temperatures are expressed in degrees Celsius.

The source of the sucrose 2,3,6,3',4'-pentaacetate (6-PAS) used in the Examples Was material supplied by Linson Limited, Swords, Dublin, containing 87.5% by weight 6-PAS and 3.74% by weight 4-PAS (sucrose 2,3,4,3',4'-pentaacetate). All references to 6-PAS in the Examples relate to the amount of 6-PAS and 4-PAS ("total PAS") used, allowing for the impurities present in the raw material, and molar equivalents are based on total PAS.

Sucralose pentaacetate (TOSPA) was assayed by HPLC using a liquid chromatograph with a Rad Pak A column (C18) 5 microns and eluting with $CH_3CN$/methanol/water (3/3/4) at 1.5 ml/minute.

Example 1 preparation of TOSPA by chlorination of 6-PAS with thionyl chloride and benzyltriethylammonium chloride (BETEC)

6-PAS (20g) was slurried in toluene (40 ml) and BETEC (2.5g) Was added. Thionyl chloride (10.6 ml; 4ME) was then added. The reaction mixture was stirred at ambient temperature for 30 minutes and was then heated to reflux (105°) over 45–60 minutes and held at reflux for 3 hours. The mixture was then cooled to 30° and water (10 ml) was added. After cooling for 30 minutes at 15°–20° the product was collected by filtration, washed with toluene (25 ml) and water (25 ml) and dried in vacuo at 45°. Yield 21.9g; 82.3% TOSPA; molar yield 85.1%

Example 2 Preparation of TOSPA by chlorination of 6-PAS with thionyl chloride and benzvltrimethylammonium chloride 6-PAS (1.0 g) was slurried in toluene (2.5 ml) and benzyltrimethylammonium chloride (0.3 g) was added. Thionyl chloride (0.53 ml; 4ME) was then added. The reaction mixture was stirred at ambient temperature for 30 minutes and was then heated to reflux (105°) over 45–60 minutes and held at reflux for 20 hours. The mixture was then cooled to 30° and water (1 ml) was added. After cooling for 30 minutes at 15°20° the product was collected by filtration, washed with toluene (2 ml) and water (2 ml) and dried in vacuo at 45° . Yield 0.91g; 69% TOSPA; molar yield 59.5%.

Example 3 preparation of TOSPA by chlorination of 6-PAS with thionyl chloride and BETEC In a series of experiments 6-PAS (20g) was slurried in toluene (1.5, 2, 2.5 or 3 volumes) and BETEC (2.5, 3.75 or 5 g; 0.3, 0.45 or 0.6 ME) was added. Thionyl chloride (10 6 ml; 4ME) was then added and the reaction mixture was stirred at ambient temperature for 30 minutes, then heated to reflux (105°) over 45–60 minutes and held at reflux for 2.5, 3 or 4 hours. The mixture was then cooled to 30° and water (10 ml) was added. After cooling for 30 minutes at 15°–20° the product was collected by filtration, washed with toluene (25 ml) and water (25 ml) and dried in vacuo at 45. The results were as follows:

| BETEC (g) | TOLUENE (ml) | REFLUX (H) | YIELD (g) | TOSPA (%) | MOLAR YIELD (%) |
|---|---|---|---|---|---|
| 5 | 50 | 3 | 21.4 | 82.5 | 83.4 |
| 5 | 50 | 4 | 21.2 | 80.3 | 80.4 |

-continued

| BETEC (g) | TOLUENE (ml) | RE-FLUX (H) | YIELD (g) | TOSPA (%) | MOLAR YIELD (%) |
|---|---|---|---|---|---|
| 5 | 60 | 3 | 16.5 | 84.1 | 65.6 |
| 3.75 | 30 | 3 | 21.1 | 81.7 | 81.4 |
| 3.75 | 30 | 4 | 21.5 | 80.7 | 82.0 |
| 3.75 | 40 | 3 | 21.7 | 82.6 | 84.7 |
| 3.75 | 50 | 3 | 19.3 | 76.3 | 69.6 |
| 3.75 | 50 | 4 | 20.7 | 82.4 | 80.6 |
| 3.75 | 60 | 3 | 19.4 | 79.2 | 72.6 |
| 3.75 | 60 | 4 | 18.5 | 74.5 | 65.1 |
| 2.5 | 30 | 3 | 21.6 | 81.0 | 82.7 |
| 2.5 | 30 | 4 | 22.7 | 79.5 | 85.3 |
| 2.5 | 40 | 2.5 | 20.5 | 82.8 | 80.2 |
| 2.5 | 40 | 3 | 22.2 | 81.9 | 85.9 |
| 2.5 | 40 | 4 | 16.5 | 76.9 | 59.9 |
| 2.5 | 60 | 4 | 20.4 | 82.2 | 79.2 |
| 2.5 | 60 | 3 | 21.2 | 75.6 | 75.7 |

The results indicate that the most economical and efficient reaction conditions comprise 4 ME thionyl chloride and 0.3 ME BETEC in two volumes of toluene, heated at reflux for 3 hours.

Example 4 preparation of TOSPA

Following the procedure described in Example 3, 6-PAS (20 g), BETEC (2.5 g) and thionyl chloride (10.6 ml) were refluxed for 2.5 hours in toluene (40 ml). The reaction mixture was then cooled to 5°, water (10 ml) was added and the product was collected by filtration to give a crude yield of 21.2 g containing 82.3% TOSPA; molar yield 82%.

Example 5 preparation of TOSPA

6-PAS (200 g) and BETEC (25 g; 0.3 ME) were slurried in toluene (400 ml). The mixture was cooled to below −5° (bath at −20°) and then thionYl chloride (106 ml; 4ME) was added over 30 minutes with good stirring. The mixture was warmed to ambient temperature over 10 minutes and stirred for a further 30 minutes. The solution was heated to reflux (105°) over one hour and held at reflux for 3 hours. Toluene (200 ml) was then added and the mixture was cooled to 70°, then water (100 ml) was added. The mixture was stirred for 5 minutes and then allowed to settle. The organic layer was washed with sodium hydroxide solution (10%, 120 ml) and water (100 ml). Toluene (200 ml) was distilled from the organic Phase under reduced pressure at 50° before cooling the mixture to 15°. After 45 minutes the crystalline solid was filtered off, washed with toluene (250 ml) and then dried at 50° in vacuo.

In four similar runs, crude yields of 203.2 g, 203.3 g, 200.1 g and 202.0 g were obtained, containing 82 3%, 83.1% 81.1% and 81.0% TOSPA, respectively (molar yields of 79.2%, 80.0%, 76.9% and 77.5%).

In a parallel comparative experiment, 6-PAS (110 g) was treated with thionyl chloride (72.2 ml; 5.5ME) and triphenyl phosphine oxide (TPPO, 55.3 g) in toluene (220 ml) under similar conditions, except that the reflux time was 2.5 hours. The product was worked up in the same way to give a crude yield of 100.4 g, containing 82.0% TOSPA (molar yield 77.8%). The reaction was faster but used larger amounts of the chlorinating agents per unit weight of 6-PAS (0.503 g TPPO and 0.66 g thionyl chloride per gram of 6-PAS, compared with 0.125 g BETEC and 0.53 g thionyl chloride per gram of 6-PAS).

Example 6 preparation of TOSPA

6-PAS (200 g) was placed in a reaction flask and covered with toluene (300 ml). BETEC (25 g: 0 3ME) was immediately washed in with toluene (100 ml). Thionyl chloride (106 ml; 4ME) was then added over a period of 5 to 15 minutes during which the temperature rose from 18° to 25°. The reaction mixture was then stirred at ambient temperature for 30 minutes and was then brought to reflux (105°) over one hour. The mixture was then heated under reflux for 4 hours and was then cooled to about 30° and water (100 ml) was then added. The suspension was cooled to 15° and stirred at this temperature for 30 minutes. The product was then collected, washed with toluene (250 ml), slurried with sodium hydrogen carbonate solution (5%, 250 ml) and finally washed with water (250 ml). The crude TOSPA was dried in vacuo at 45° to give a yield of 202 g (84.2% TOSPA, toluene solvated) molar yield 80.6%.

Example 7 Larger scale preparation of TOSPA by chlorination of 6-PAS with thionyl chloride and BETEC 6-PAS (750 g) and BETEC (93.75 g; 0.3 ME) were slurried in toluene (1500 ml) and the mixture was cooled to −10°. Thionyl chloride (397.5 ml; 4ME) was added over 30 minutes with stirring. The mixture was then warmed to ambient temperature over about 10 minutes and kept at this temperature for 30 minutes. The solution was then heated to reflux (105°) over one hour and then held at reflux for 4 hours. The mixture was then cooled to about 40° and water (375 ml) was added. Cooling was continued to between 0° and 5° and the mixture was stirred at low temperature for 45 minutes after which the product was collected and filtered. The filter cake was washed with isopropanol (937 ml) to remove most of the colour and the damp cake was recrystallised from isopropanol (3000 ml). The recrystallised product was washed with isopropanol (375 ml) and dried in vacuo at 45°.

In three similar runs, yields of 641 g, 643 g and 604 g were obtained, containing 96.6%, 92.9% and 95.2% TOSPA, repectively (molar yields of 78.3%, 75.5% and 72.7%).

Example 8 preparation of sucrose 6-acetate persulphite and isolation from free base pyridine Sucrose 6-acetate (ca 88% pure; 11 g) in pyridine (50 ml) was added dropwise over one hour to a cold (0°) solution of thionyl chloride (15 ml; 7ME) in pyridine (20 ml), maintaining the temperature below 10°. The semi-solid mixture was then stirred for 30 minutes at 5°. Petroleum ether was then added and stirring was continued for a further 30 minutes. The precipitate (containing the sucrose 6-acetate persulphite and pyridine hydrochloride) was isolated by filtration and dried in vacuo for 2 hours (weight 60 g).

Example 9 preparation of sucrose 6-acetate persulphite and isolation from free base pyridine Sucrose 6-acetate (ca 88% pure; 14 g), thionyl chloride (12 ml; 4.5 ME) and pyridine (22 ml; 10ME) were reacted in acetonitrile (70 ml) as solvent at 10° for one hour. A gelatinous precipitate was formed comprising sucrose 6-acetate persulphite. Water (50 ml) was then added and the mixture was filtered, washed with water and dried.

Example 10 Chlorination of sucrose 6-acetate persulphite with thionyl chloride and BETEC to provide sucralose 6-acetate To sucrose 6-acetate persulphite (12.3 g) from Example 9, in 1,2-dichloroethane (50 ml), was added thionyl chloride (6.6 ml; 3.75ME), followed by BETEC (1.1 g; 0.2ME). The reaction mixture was heated slowly to reflux (83° C.) and held at reflux for 16 hours, then cooled to room temperature. To the cooled mixture was added ammonium hydroxide solution (0.880 SG, 7 ml) and water (14 ml) and the mixture was stirred vigorously for 3 hours at room temperature. Concentrated hydrochloric acid was then added slowly to neutralise the mixture, which was then concentrated to a residue by evaporation. The residue was dissolved in ethyl acetate (30 ml) and the solution was washed with water (6 ml). The organic layer was filtered through charcoal, washing the filter bed with further ethyl acetate (20 ml). Diethyl ether was added to the filtrate until a little cloudiness remained and the mixture was then stirred overnight during which time the sucralose 6-acetate crystallised. The crystalline material was collected by filtration and dried to provide 2.6 g sucralose 6-acetate.

Example 11 preparation of raffinose persulphite and isolation from free base pyridine (comparative)

Thionyl chloride (7 ml) was added to pyridine (22.5 ml) and the solution was cooled to 0° using an ice bath. Raffinose (5 g) was dissolved in pyridine (27.5 ml) and the solution was added dropwise over 30 minutes. The mixture was stirred at 0° for 30 minutes, then petroleum ether (40°–60°, 50 ml) was added and the mixture was stirred for a further 30 minutes. The precipitate, comprising raffinose persulphite and pyridine hydrochloride, was separated by filtration, washed with petroleum ether (50 ml) and dried in vacuo at ambient temperature for two hours.

Example 12 Chlorination of raffinose persulphite with thionyl chloride, without addition of a salt of formula I, to provide TCR (comparative)

The dry product of Example 11 was dissolved in 1,2-dichloroethane (50 ml) and thionyl chloride (7.5 ml) and the solution was heated under reflux for 16 hours, and then concentrated to a solid residue by evaporation. To the residue was added 0.880 ammonia/methanol. 1:1 (100 ml) and the mixture was warmed to 50° for 30 minutes before being concentrated to a solid (4.3 g; 59% TCR determined by HPLC as described in Example 14; molar yield 44%).

Example 13 preparation of raffinose persulphite and isolation from free base pyridine A solution of anhydrous raffinose (15 g) in pyridine (65 ml) was cooled to −10° and to this, a solution of thionyl chloride (24.1 ml; 6.5 ME) in cold pyridine (35 ml) was added dropwise with stirring over a period of 30 minutes, maintaining the temperature in the range −5° to 5°. Methanol (100 ml) was then added, at first dropwise, keeping the temperature below 10°, and the mixture was stirred for a further 15 minutes. The precipitated raffinose persulphite was isolated by filtration, washed with methanol (100 ml), then ether (2×100 ml) and dried in vacuo over P2O5 overnight to provide 21.8 g of the intermediate.

Example 14 Chlorination of raffinose persulphite with thionyl chloride and BETEC, to provide TCR The dry product of Example 13 was suspended in 1,2-dichloroethane (65 ml) at room temperature. Thionyl chloride (11.9 ml; 5.5ME) was added, followed by BETEC (1.36 g; 0.2ME), and the mixture was warmed slowly to reflux (83°). After 12 hours at reflux, the mixture was concentrated to 30 ml and poured cautiously into ice cold 0.880 SG ammonia solution (100 ml). The mixture was stirred vigorously at 50° for one hour. After cooling to room temperature, the organic phase was separated and washed with an equal volume of water. The combined aqueous layers were saturated with sodium chloride and extracted with butanone (4×125 ml). The combined extracts were neutralised using Duolite DMF ($H^{30}/OH^{31}$) resin and filtered. The filtrate was concentrated to a foam (13.0g) which was dissolved in water (50 ml) and treated with decolourising charcoal at 50°. The filtered solution was concentrated to 25 ml, seeded and allowed to crystallise. The isolated yield of TCR was 8.5 g, molar yield 49% (determined by HPLC using a liquid chromatograph with a PREP-PAK 500/C18 column and eluting with acetonitrile:water 20:80).

Example 15 preparation of sucrose persulphite and isolation from free base pyridine To sucrose (12 g) in pyridine (180 ml) was slowly added thionyl chloride (12 ml; 4.5ME), keeping the temperature below 10°. To the resulting mixture was then added toluene (40 ml) and the precipitate, comprising the sucrose persulphite, was filtered off. The solid material was washed sequentially with toluene, methanol and ether, then dried under vacuum at room temperature to give a dry solid (25 g).

Example 16 Chlorination of sucrose persulphite with thionyl chloride and BETEC, to provide (-1 4,6,1',6'-tetrachloro-4,6,1',6'-tetradeoxy galactosucrose A portion of the dry solid product of Example 15 (4 g) was suspended in toluene (30 ml) and thionyl chloride (2.6 ml) was added followed by BETEC (0.4 g). The mixture was heated to 105° and refluxed for 4 hours. The mixture was then cooled to room temperature and 0.880 ammonia/methanol 1:1 (50 ml) was added. The mixture was then warmed to 50° for 2 hours and then evaporated to give a residue which was then partitioned between water and ethyl acetate. The organic phase was then filtered and the filtrate was evaporated to give a syrupy residue (1.42 g), containing 81% 4,6,,1',6'-tetrachloro-4,6,1',6-tetradeoxy galacto sucrose (determined by HPLC using a liquid chromatograph with a Steel resolve CC18 5 micron column and eluting with acetonitrile:water 28:72); molar yield 50%.

Example 17 preparation of sucralose

A sample of TOSPA from Example 7 (50 g) was taken up in methanol (125 ml) and sodium methoxide (0.5 g) was added. The mixture was then stirred at room temperature for 1.5 hours under vacuum. The resulting solution was neutralised by stirring with Amberlite IRC 50 ($H^{30}$) resin (7.5 g). The resin was then removed by filtration and washed with methanol (25 ml). The filtrate and wash were then stirred with decolourising charcoal (2 g) and celite (2g) for 15 minutes, then the solution was clarified by filtration and concentrated to a froth in vacuo. Sucralose was crystallised from ethyl acetate (100 ml), filtered, washed with ethyl acetate (25 ml) and dried in vacuo at 40° for 12 hours. Yield 26.6 g (94%).

Example 18 preparation of sucralose

The product of Example 8 was washed sequentially with toluene, methanol and ether to remove most of the pyridine hydrochloride, then dried in vacuo at room temperature for 2 hours. To a portion of the dry sucrose 6-acetate persulphite (10 g), in 1,1,2-trichloroethane (40 ml), was added thionyl chloride (5 ml: 3.5ME), followed by BETEC (0.9 g; 0.2ME). The reaction mixture was heated slowly to reflux (112° C.) and held at reflux for 1.5 hours, then cooled to room temperature. To the cooled mixture was added ammonium hydroxide solution (0.880 SG, 6 ml) and water (12 ml) and the mixture was stirred vigorously for 3 hours at room temperature. Concentrated hydrochloric acid was then added slowly to neutralise the mixture, which was then concentrated to a syrupy residue by evaporation. The syrup was then acetylated in the conventional manner, with acetic anhydride in pyridine. Sucralose pentaacetate (TOSPA) was separated from the reaction mixture by crystallisation, taken up in methanol and deacetylated by treatment with sodium methoxide in the conventional manner, to yield sucralose (2.1 g).

We claim:

1. In the process for the chlorination of sucrose and partly protected sucrose derivatives by reaction of unprotected hydroxyl groups with thionyl chloride to form a persulphite followed by decomposition of the sulphite groups to form chlorosulphites, displacement of the chlorosulphite groups and insertion of chlorine atoms at one or more positions, the improvement consisting in that formation and displacement of the chlorosulphite groups and insertion of chlorine atoms is effected by reaction with thionyl chloride in an inert solvent in the presence of a quaternary salt of the formula:

$$N^+R^1R^2R^3R^4\ Cl^- \qquad (I)$$

wherein $R^1$, $R^2$ and $R^3$, which may be the same or different, each represent a lower alkyl group, and $R^4$ represents an arylalkyl group with at least seven carbon atoms; and, when the sucrose or partly protected sucrose derivative has more than three unprotected hydroxyl groups, the process comprises the following stages:

(a) reaction of the sucrose or partly protected sucrose derivative with thionyl chloride in the presence of pyridine to form a persulphite;

(b) isolation of the polysulphite to remove free pyridine; and (c) reaction of the isolated polysulphite with thionyl chloride in an inert solvent or suspension medium in the presence of a quaternary salt of the general formula (I).

2. The process of claim 1, in which the quaternary salt of formula I is one in which $R^4$ represents a benzyl group.

3. The process of claim 1, in which the quaternary salt of formula I is one in which $R^1$, $R^2$ and $R^3$ each represent a methyl, ethyl or propyl group.

4. The process of claim 1, in which the amount of quaternary salt of formula I used in the reaction medium is about 0.2 to 0.4 molar equivalent, based on the sucrose or sucrose derivative.

5. The process of claim 1, in which the thionyl chloride used in stage is present in a molar excess.

6. The process of claim 5, in which the thionyl chloride is present in about 10% excess.

7. The process of claim 1 which, when the partly protected sucrose derivative has less than four unprotected hydroxyl groups, comprises reaction of the partly protected sucrose derivative with thionyl chloride in an inert solvent or suspension medium in the presence of a quaternary salt of the formula (I), without isolation of the polysulphite.

8. The process of claim 7, in which the thionyl chloride used is present in a molar excess.

9. The process of claim 8, in which the thionyl chloride is present in an amount of about 1.25 to 1.75 ME per free hydroxy group.

10. The process of claim 9, in which the thionyl chloride is present in an amount of about 1.3 to 1.4 molar equivalents per free hydroxyl group.

11. The process of claim 1, in which the partly protected sugar derivative is a sucrose 2,3,6,3',4'-pentaester.

12. A process for the preparation of sucralose, comprising chlorination of a sucrose 2,3,6,3',4'-pentaester by a process according to claim 11 to form a sucralose pentaester, and de-esterification of the sucralose pentaester to form sucralose.

13. A process according to claim 1, in which the partly protected sucrose derivative is a sucrose 6-ester.

14. A process for the preparation of sucralose, comprising chlorination of a sucrose 6-ester by a process according to claim 13 to form a sucralose 6-ester, esterification of this intermediate to form a sucralose pentaester and de-esterification of the pentaester to form sucralose.

* * * * *